United States Patent [19]

Meijer et al.

[11] 4,154,965

[45] May 15, 1979

[54] PROCESS FOR THE PREPARATION OF RESORCINOL OR ALKYLSUBSTITUTED DERIVATIVES THEREOF

[75] Inventors: Peter J. N. Meijer, Munstergeleen, Netherlands; Annita M. F. Vanholsaet, Dilsen, Belgium; Erik T. M. Wolters, Schinnen, Netherlands

[73] Assignee: Stamicarbon, B.V., Geleen, Netherlands

[21] Appl. No.: 847,652

[22] Filed: Nov. 1, 1977

[30] Foreign Application Priority Data

Nov. 5, 1976 [NL] Netherlands ................... 7612281

[51] Int. Cl.$^2$ ............................................. C07C 39/08
[52] U.S. Cl. .................................................. 568/772
[58] Field of Search ............... 260/621 R, 621 D, 625, 260/586 C; 568/772, 771

[56] References Cited

U.S. PATENT DOCUMENTS

| | | | |
|---|---|---|---|
| 3,627,833 | 12/1971 | Tobis | 260/586 C |
| 3,932,511 | 1/1976 | Schaafsma et al. | 260/586 C |
| 3,950,438 | 4/1976 | Schaafsma et al. | 260/621 R |
| 4,018,833 | 4/1977 | Muller et al. | 260/621 R |

*Primary Examiner*—Werren B. Lone
*Attorney, Agent, or Firm*—Cushman, Darby & Cushman

[57] ABSTRACT

A two-stage process for the conversion of certain esters of delta-keto carboxylic acids to the corresponding resorcinol is described, using a first vapor phase stage for cyclization to a dihydroresorcinol followed by a second liquid phase dehydrogenation, in the presence of unconverted ester, to form the resorcinol product.

6 Claims, No Drawings

PROCESS FOR THE PREPARATION OF RESORCINOL OR ALKYLSUBSTITUTED DERIVATIVES THEREOF

This invention relates to an improved process for the preparation of resorcinol, or alkyl-substituted resorcinols, starting from delta keto esters.

BACKGROUND OF THE INVENTION

The basic processes for this synthesis are, in general, already known.

In U.S. Pat. No. 3,950,438 (the disclosure thereof is incorporated herein by reference), such a process is described wherein delta keto esters are converted in one step into the corresponding resorcinol; (however, variable amounts of the corresponding dihydro resorcinol and also some phenol are nonetheless formed as by-product therein). Furthermore, U.S. Pat. No. 3,932,511 (the disclosure thereof is incorporated herein by reference) has described a process for the cyclization of delta keto esters to form the corresponding dihydroresorcinol.

The overall yields obtained in said U.S. Pat. No. 3,950,438 are good, but not as high as is to be desired. While high yields for the production of the dihydroresorcinols are provided in U.S. Pat. No. 3,932,511, that product must still be dehydrogenated to obtain the desired resorcinol.

It is also known that such a dehydrogenation of dihydroresorcinols can be effected by conducting that reaction in a solvent by the procedure described in the published Netherlands patent application No. 75 09211. In this operation a rather high yield can be obtained, provided that di-, tri- or tetraethyl-glycol dialkylethers is used as solvent. However, these solvents are rather expensive, and their use as reaction media thus impose a substantial price for obtaining a good yield.

OBJECT OF THE INVENTION

It is a principal object of this invention to provide an improved process for converting delta-keto aliphatic acid esters into resorcinol by providing a two-stage process which avoids the use of expensive solvents.

DESCRIPTION OF THE INVENTION

By contrast to the practice of the prior art, in the process of the present invention for preparing resorcinol or alkyl-resorcinols, the total delta keto ester starting material is first only partly converted to the corresponding dihydroresorcinol in a vapor phase first stage reaction, at an elevated temperature (with, of course, simultaneous release of the alcohol originally present in the ester group). The resulting dihydroresorcinol is then, in a liquid phase second stage, in the presence of the unconverted keto ester, subjected to a dehydrogenation treatment to form the desired resorcinol. This product may then be readily recovered from the resulting reaction mixture.

By use of this procedure, higher overall yields of the resorcinol product are realized, and the use of the above-mentioned expensive solvents or reaction additives is no longer required.

Also, by use of the process of this invention, the second stage dehydrogenation step can be carried out at higher temperatures in the liquid phase than in the previously known dehydrogenation process (when conducted in the presence of the most suitable glycolethers). The delta keto esters used as the reaction solvent in the present invention have a higher boiling point than these glycolethers. This is an important advantage because the higher temperatures thus permitted cause the reaction to proceed faster. Another advantage of the present process is that less phenol is formed as a by-product in the liquid phase dehydrogenation than in the previously known dehydrogenation, as mentioned above.

In the process according to the present invention, various keto esters can be employed as starting material, i.e., the same class of starting materials, as used in the aforementioned U.S. Pat. No. 3,950,438; in particular, those keto esters satisfying the general formula:

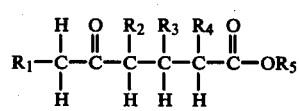

In this formula, $R_1$, $R_2$, $R_3$ and $R_4$, independently represent either a hydrogen atom or a lower alkyl group of up to 6 carbon atoms, with the proviso that the total number of carbon atoms in the substituents $R_1$, $R_2$, $R_3$ and $R_4$ is at most 12. The symbol $R_5$ itself denotes a hydrocarbon group of at most 12 carbon atoms; for instance, $R_5$ may be an alkyl, cycloalkyl, or monocyclic or bicyclic aryl or arylalkyl group containing up to 12 carbon atoms.

As product of the process there is accordingly obtained a resorcinol of the following general formula (with $R_1$, $R_2$, $R_3$ and $R_4$ having the same meanings indicated above):

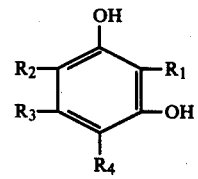

In the process according to this invention, the initial vapor phase cyclization of the delta keto ester can itself be carried out in various known ways. Thus, the ester in the vapor phase may be passed over a fixed bed or a fluid bed of a finely divided particulate solid material with a large internal surface area, e.g., of 100 to 1500 m² per gram. Suitable solid materials for this purpose include activated carbon or magnesium oxide. Advantageously, the ester is so treated while diluted with an inert gas, e.g., nitrogen, carbon dioxide or hydrogen, such inert gas may be used in an amount of about 1 to about 15 mols per mole of ester.

Such solid material used in the cyclization may also be itself a dihydrogenation catalyst, including a metal or a compound of a metal from the 8th group or 1st sidegroup of Mendelejeff's periodic system. Particularly suitable for use as dehydrogenation catalyst are platinum, palladium and nickel. Such catalysts are usually employed on a carrier, as, e.g., carbon, silica, calcium oxide, magnesium oxide and alumina. Also see the description of suitable catalysts in U.S. Pat. No. 3,950,438. If use is made of a dehydrogenation catalyst, in the first stage of the process of this invention, then, some of the corresponding resorcinol can also be obtained in the first stage reaction product along with dihydroresorcinol.

In the practice of the present invention, the first stage cyclization reaction can be carried out very appropriately at temperatures of between 100° and 500° C. Preferably, a temperature of between about 200° and about 350° C. is employed, because then very few undesired side-reaction by-products are formed, and the desired extent of the cyclization reaction is readily achieved. In the said first stage, the keto ester is only partly converted e.g. a percentage in the range of 3%–65%.

The resulting gaseous reaction mixture can then be condensed to the liquid state, by cooling, whereupon the $R_5OH$ alcohol by-product formed in the cyclization reaction can be removed by distillation, if so required.

The resulting liquid reaction product containing both unconverted keto ester and the dihydroresorcinol product formed are then subjected to dehydrogenation conditions, such that the first stage dihydroresorcinol product is dehydrogenated to the corresponding resorcinol. This can be very suitably realized in the second stage of this process by contacting the first stage liquid reaction product at an elevated temperature with a dehydrogenation catalyst, for the required amount of time.

For this purpose, the above-mentioned dehydrogenation catalysts and carrier materials can again be employed. Preferably, palladium or a palladium-compound are used as dehydrogenation catalyst in the dehydrogenation step.

The second stage reaction temperature can be chosen within various ranges, e.g., between 150° and 300° C., but is preferably between about 170° to about 250°. In this latter, preferred, temperature range, the dehydrogenation reaction not only gives a desirably high yield but also proceeds at an acceptably fast rate.

The pressure used is by itself not critical; it is only necessary that it be sufficiently high, depending on the temperature, that in the dehydrogenation reaction the liquid reaction phase will be maintained.

Upon completion of the liquid phase dehydrogenation step, the catalyst is preferably first removed from the reaction mixture, e.g., by filtration. The resorcinol formed can then be readily recovered from the reaction mixture by distillation. The unconverted delta keto ester residue left after this distillation can, of course, be recycled and re-used as feedstock to the first stage of the process.

EXAMPLES OF THE INVENTION

The invention will now be further elucidated and appreciated by reference to the following examples.

EXAMPLE I

A gaseous mixture of hydrogen and the methylester of 4-oxopentane-1-carboxylic acid (in a molar ratio of 10:1) was passed downwards, for 21 hours, through a vertically disposed tubular reactor having a diameter of 18 mm and a length of 400 mm. The gaseous mixture had been obtained by evaporation of liquid methylester of 4-oxopentane-1-carboxylic acid and mixing the vapor with hydrogen.

The reactor contained two zones of approximately 35 milliliters of inert material, separated from each other by a zone of 30 milliliters of carbon (carbonized peat) molded into rods of 0.9 mm diameter and 2–3 mm length (bulk density 0.35 gram per milliliter; internal surface area 800 m² per gram). The space velocity was 0.2 milliliters (760 mm Hg, 20° C.) of methylester per milliliter of carbon per hour.

The temperature of the carbon was kept at 300°–302° C. by means of a heating shell.

An amount of 6.15 g/h of the said methylester was thus introduced into the reactor tube.

After 12 hours of operation, the resulting gas mixture was passed for 9 hours through a receiving vessel cooled to −20° C. The condensed liquid product thus obtained (54.4 g) contained 5.8% wt. of dihydroresorcinol, a slight amount of methanol and 92.6% wt. of methylester of 4-oxopentane-1-carboxylic acid.

From this mixture the methanol was removed by distillation at 22 mm Hg. Next, via a dropping funnel, the liquid residue was supplied, in 20 minutes time, to a reaction flask provided with a stirrer and a reflux condenser. This flask contained a suspension of 1 g of palladium-on-carbon catalyst (10% wt. of palladium) in 50 g of the methylester of 4-oxopentane-1-carboxylic acid. The temperature in the reaction flask was kept at approximately 200° C. by means of an oil bath. After introduction of the said residue was complete, the reaction mixture was kept at this temperature for another 45 minutes, with stirring.

Next, the catalyst was filtered off and the reaction mixture was analyzed gaschromatographically. The analysis showed that the mixture no longer contained dihydroresorcinol, and that 2.9 g of resorcinol had been formed, and 100.4 g of unconverted methylester remained. Based on the amount of converted methylester of 4-oxopentane-1-carboxylic acid, the yield of resorcinol amounted to 93%.

EXAMPLE II

The experiment described in Example I was repeated under the same conditions, except that this time the methylester of 3-methyl-4-oxopentane-1-carboxylic acid was employed as starting material. Instead of hydrogen, nitrogen was now used as carrier gas (10 moles of nitrogen per mole of said methylester of 3-methyl-4-oxopentane-1-carboxylic acid). An amount of 5.9 g/h of this methylester was introduced into the tubular reactor.

After 8 hours of operation, the gaseous reaction mixture from the first stage reaction was collected for 9 hours, and condensed according to the procedure described in Example I. The resulting liquid mixture (53 g) was then subjected to a distillation treatment at 12 mm Hg to remove the methanol. The liquid residue was then supplied to a suspension of 1 g of palladium-on-carbon catalyst (10% wt. of palladium) in 50 g of the methylester of 3-methyl-4-oxopentane-1-carboxylic acid, by the procedure described in Example I, whereupon the experiment was continued, likewise in the way described in Example I.

Gaschromatographic analysis of the reaction product obtained showed that 8.2 g of 4-methylresorcinol had been formed, while 91.5 g of unconverted starting product, the methylester of 3-methyl-4-oxopentane-1-carboxylic acid remained. The yield of 4-methylresorcinol, calculated to the converted amount of methylester, was therefore 91%.

In general, the process just described may be followed for the preparation of other resorcinol compounds (of the general formula mentioned above) by use of the appropriate corresponding delta keto ester (also as defined above).

The scope of this invention is accordingly limited only by the spirit and scope of the following claims.

What is claimed is:

1. In the conversion of an ester of a delta keto alkane carboxylic acid of the general formula

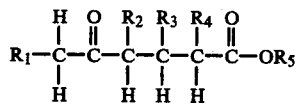

to the corresponding resorcinol, of the general formula

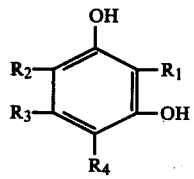

wherein $R_1$, $R_2$, $R_3$ and $R_4$, independently represent either a hydrogen atom or a lower alkyl group of up to 6 carbon atoms, with the proviso that the total number of carbon atoms in the substituents $R_1$, $R_2$, $R_3$ and $R_4$ is at most 12, and the symbol $R_5$ represents a hydrocarbon group of up to 12 carbon atoms, the improvement of a two-stage process consisting essentially in that (a) the said keto ester is first cyclized in the vapor phase at an elevated temperature between about 100° and 500° C., to yield at least in part the corresponding dihydroresorcinol; (b) the resulting dihydroresorcinol-containing mixture is condensed to form a liquid phase; and then (c) in the presence of (i) non-converted keto ester and (ii) a dehydrogenation catalyst of a metal of the group platinum, palladium and nickel, the said dihydroresorcinol is dehydrogenated at elevated temperature between about 150° and 300° C. and under substantial pressure, to maintained in said liquid phase, to form said resorcinol product.

2. The process of claim 1, wherein said step (a) is conducted at a temperature between about 200° C. and 350° C.

3. The process of claim 1, wherein in said step (a) 3%–65% of the starting amount of said keto ester is converted.

4. The process of claim 1, wherein after said step (b) the alcohol by-product from the cyclization reaction is distilled off.

5. The process of claim 1, wherein said elevated temperature in step (c) is between about 170° and 250° C.

6. The process of claim 1, wherein the dihydrogenation catalyst contains palladium.

* * * * *